United States Patent
Wheeler et al.

(10) Patent No.: US 7,612,082 B2
(45) Date of Patent: Nov. 3, 2009

(54) PROSTAGLANDIN $EP_4$ ANTAGONISTS

(75) Inventors: Larry A. Wheeler, Irvine, CA (US);
Michael E. Garst, Newport Beach, CA (US); Yanbin Liang, Irvine, CA (US); David F. Woodward, Lake Forest, CA (US); Achim H.-P. Krauss, San Marcos, CA (US); Robert M. Burk, Laguna Beach, CA (US); Yariv Donde, Dana Point, CA (US); Mark Holoboski, Laguna Niguel, CA (US); David W. Old, Irvine, CA (US); June Chen, San Juan Capistrano, CA (US)

(73) Assignee: Allergan, Inc., Irvine, CA (US)

( * ) Notice: Subject to any disclaimer, the term of this patent is extended or adjusted under 35 U.S.C. 154(b) by 649 days.

(21) Appl. No.: 10/976,442

(22) Filed: Oct. 28, 2004

(65) Prior Publication Data
US 2006/0094742 A1 May 4, 2006

(51) Int. Cl.
*A61K 43/42* (2006.01)
(52) U.S. Cl. .................. 514/284; 514/183; 514/913
(58) Field of Classification Search .................. 514/290
See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 4,812,448 A * | 3/1989 | Knepper | 514/178 |
| 6,369,089 B1 | 4/2002 | Burk et al. | |
| 6,956,057 B2 * | 10/2005 | Woodward et al. | 514/530 |
| 2005/0147648 A1 * | 7/2005 | Gierhart | 424/439 |
| 2006/0030606 A1 * | 2/2006 | Old et al. | 514/365 |

FOREIGN PATENT DOCUMENTS

WO  WO00/15608  3/2000
WO  WO01/49661  7/2001

OTHER PUBLICATIONS

Suzawa et al., The Role of Prostaglandin E Receptor Subtypes (EP1, EP2, EP3, and EP4) in Bone Resporption: An Analysis Using Specific Agonists for the Respective EPs, 2000, Endocrinology, vol. 141, No. 4, pp. 1554-1559.*
Database Chemcats, STN; AN: 2003:2283722; Apr. 25, 2003, XP 002368290.
Database Registry, STN; RN: 468093-79-0; Oct. 31, 2002, XP 002368291.
Database Registry, STN; RN: 468713-77-1; Nov. 1, 2002, XP 002368292.
Database Registry, STN; RN: 339310-56-4; Jun. 4, 2001, XP 002368293.

* cited by examiner

*Primary Examiner*—Ardin Marschel
*Assistant Examiner*—Meghan Finn
(74) *Attorney, Agent, or Firm*—Kevin J. Forrestal; Allergan, Inc.

(57) ABSTRACT

Disclosed herein are methods and compositions related to compound 1 or compound 2

Compound 1

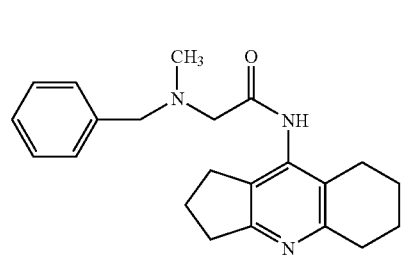

Compound 2

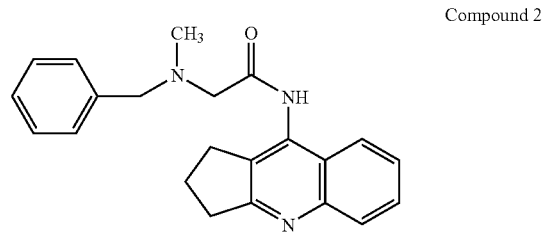

or pharmaceutically acceptable salts, or prodrugs thereof, which are antagonists of a prostaglandin $EP_4$ receptor, or are prostaglandin $EP_4$ antagonists.

2 Claims, No Drawings

PROSTAGLANDIN EP₄ ANTAGONISTS

BACKGROUND OF THE INVENTION

1. Field of the Invention

This disclosure relates to pharmaceutical compositions and medical treatments. In particular, this disclosure relates to the use of prostaglandin $EP_4$ antagonists in said compositions and treatments.

2. Description of the Related Art

Prostaglandin $EP_4$ antagonists are believed in the art to have a number of useful medicinal properties. WO0149661 discloses compounds which "strongly bind to $PGE_2$ receptors (in particular, subtype $EP_4$), so that the [compounds] are expected to be useful in the prevention and/or treatment of immunopathy, asthma, bone dysplasia, nerve cellular death, lung failure, hepatopathy, acute hepatitis, nephritis, renal failure, hypertension, myocardial ischemia, systemic inflammatory reaction syndrome, septicemia, hemophagocytosis syndrome, macrophage activation syndrome, Still disease, Kawasaki disease, burn, systemic granuloma, ulcerative colitis, Crohn disease, hypercytokinemia at dialysis, multiple organ failure, shock, sleep disorder, platelet aggregation and so on." WO0149661 also discloses that "compounds which can bind on $EP_4$ subtype receptor strongly are expected to be useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus etc., and rejection after organ transplantation etc.), asthma, abnormal bone formation, neuronal cell death, lung failure, liver damage, acute hepatitis, nephritis, renal insufficiency, hypertension, myocardiac ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc. Further, it is thought that $EP_4$ subtype receptor relates to sleeping disorder and blood platelet aggregation, so such compounds are expected to be useful for the prevention and/or treatment of these diseases."

WO0015608 discloses "because of binding strongly to PGE2 receptors (in particular, subtype $EP_4$), the compounds [disclosed in the reference] are useful in preventing and/or treating immunologic diseases (autoimmune diseases such as amyotrophic lateral sclerosis (ALS), rejection reactions following organ transplantation, etc.), asthma, bone dysplasia, nerve cell death, lung failure, liver failure, etc. Also, these compounds participate in sleep disorder and platelet agglutination and, therefore, are useful in treating diseases relating thereto." WO0015608 also discloses "compounds of the present invention of formula (I) bind strongly on subtype $EP_4$ and therefore are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burn, systemic granuloma, ulcerative colititis, Crohn's diseases, hypercytokinemia at dialysis, multiple organ failure, shock, etc. They are also related with sleeping disorders and platelet coagulations, and therefore they are thought to be applicable to these diseases."

In citing the foregoing references, and other references cited herein, applications make no admission as to whether any of said references constitutes prior art. Rather, the determination of what constitutes prior art is a legal decision made on the basis of the dates said references were made available to the public, the authors or inventors of said references, and the effective filing date of the disclosure made herein.

BRIEF DESCRIPTION OF THE INVENTION

Disclosed herein are methods and compositions related to compound 1 or compound 2

Compound 1

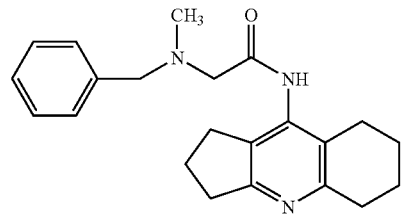

Compound 2

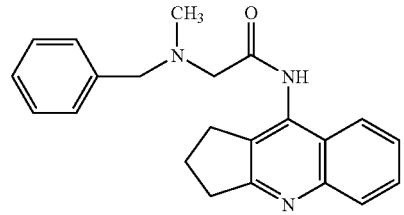

or pharmaceutically acceptable salts, or prodrugs thereof (all of which are referred to hereafter, collectively or individually, as "compound 1" or "compound 2", or "compounds"), which are antagonists of a prostaglandin $EP_4$ receptor, or are prostaglandin $EP_4$ antagonists.

DETAILED DESCRIPTION OF THE INVENTION

Compounds 1 and 2 are used in a medical sense to treat or prevent a condition or disease which is mediated by a prostaglandin $EP_4$ receptor.

A condition or disease which is mediated by the prostaglandin $EP_4$ receptor is one in which the binding or lack of binding, or the agonism or antagonism of the prostaglandin $EP_4$ receptor, causes or contributes to the cause of a disease or condition, or a symptom thereof.

These compounds have several medical uses, including treatment of skeletal disorders, including osteoporosis and bone dysplasia; cancer, including colorectal cancer; immunological disorders, including but not limited to Sjoegren's syndrome, multiple sclerosis, amyotrophic lateral sclerosis, rheumatoid arthritis, and lupus erythematosus; neurodegenerative disorders, including stroke; ocular diseases, including dry eye, neurodegenerative conditions, glaucoma, non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulatiori, radiation retinopathy, epiretinal membranes, proliferative diabetic retinopathy, branch retinal vein occlusion, anterior ischemic optic neuropathy, non-retinopathy diabetic retinal dysfunction, and retinitis pigmentosa; pulmonary respiratory diseases, including asthma and chronic obstructive pulmonary disorder; hepatic diseases including hepatitis; myocardial ischemia; renal disease, including dialysis adjunct and nephritis; systemic hypertension; septicemia; sleep disorders; shock, including multiple organ failure; fibromyalgia; inflammatory bowel disorder; gastrointestinal disease, including irritable bowel syndrome, diarrhea, colitis, ulcerative colitis, inflammatory bowel disease; Still's disease; Kawasaki's disease; Crohn's disease; hemophagocytosis syndrome; dermatological disorders, including dermatitis, psoriasis, and acne; systemic granuloma; burns and scalds; pain, including migraine; and antipyrexia.

In one embodiment these compounds are used to treat or prevent skeletal disorders including osteoporosis and bone dysplasia.

In another embodiment these compounds are used to treat or prevent cancer including colorectal cancer.

In another embodiment these compounds are used to treat or prevent immunological disorders, including but not limited to Sjoegren's syndrome, multiple sclerosis, amyotrophic lateral sclerosis, rheumatoid arthritis, and lupus erythematosus.

In another embodiment these compounds are used to treat or prevent neurodegenerative disorders, including stroke.

In another embodiment these compounds are used to treat or prevent ocular diseases including dry eye, and glaucoma.

In another embodiment these compounds are used for neuroprotection in an ocular disease such as glaucoma, non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, and retinitis pigmentosa.

In another embodiment these compounds are used to treat or prevent pulmonary respiratory diseases such as asthma and chronic obstructive pulmonary disorder.

In another embodiment these compounds are used to treat or prevent hepatic diseases including hepatitis.

In another embodiment these compounds are used to treat or prevent myocardial ischemia.

In another embodiment these compounds are used to treat or prevent renal disease including use as a dialysis adjunct and the treatment or prevention of nephritis.

In another embodiment these compounds are used to treat or prevent systemic hypertension.

In another embodiment these compounds are used to treat or prevent septicemia.

In another embodiment these compounds are used to treat or prevent sleep disorders.

In another embodiment these compounds are used to treat or prevent shock including multiple organ failure.

In another embodiment these compounds are used to treat or prevent fibromyalgia.

In another embodiment these compounds are used to treat or prevent gastrointestinal disease, including irritable bowel syndrome, diarrhea, colitis, inflammatory bowel disease, and ulcerative colitis.

In another embodiment these compounds are used to treat or prevent Still's disease.

In another embodiment these compounds are used to treat or prevent Kawasaki's disease.

In another embodiment these compounds are used to treat or prevent Crohn's disease.

In another embodiment these compounds are used to treat or prevent hemophagocytosis syndrome.

In another embodiment these compounds are used to treat or prevent dermatological disorders including dermatitis, psoriasis, and acne.

In another embodiment these compounds are used to treat or prevent systemic granuloma In another embodiment these compounds are used to treat burns and scalds.

In another embodiment these compounds are used to treat or prevent pain.

In another embodiment these compounds are used to treat or prevent antipyrexia.

Compositions, formulations, dosage forms, medicaments, kits, and pharmaceutical products comprising compound 1 for the medical uses described herein are also contemplated.

A "pharmaceutically acceptable salt" is any salt that retains the activity of the parent compound and does not impart any additional deleterious or untoward effects on the subject to which it is administered and in the context in which it is administered compared to the parent compound.

Pharmaceutically acceptable salts of acidic functional groups may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Those skilled in the art will readily understand that for administration the compounds disclosed herein can be admixed with pharmaceutically acceptable excipients which, per se, are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgement of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edentate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The following Examples describe methods of synthesizing the compounds shown herein to be a prostaglandin $EP_4$ antagonist. Other methods may also be used.

These compounds can be purchased from several companies including ChemDiv., Inc, San Diego, Calif.; Interchim, Muntlucon, Cedex, 03103, France; Ambinter, Paris, France; and ChemBridge Corporation, San Diego, Calif.

Determination of the effect of compound 1 on the activity of Prostaglandin E2 on the induced calcium signal: HEK-293 (EBNA) cells, stably expressing cDNAs for the human $EP_4$ receptor and Gqs5 proteins, were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed twice with HBSS-HEPES buffer (Hanks Balanced Salt Solution without bicarbonate and phenol red, 20 mM HEPES, pH 7.4) using a Denley Cellwash plate washer (Labsystems; Franklin, Mass.). After 45-60 min of dye-loading in the dark using the calcium-sensitive dye Fluo-4 AM, at a final concentration of 2 µM, plates were washed four times with HBSS-HEPES buffer to remove excess dye and leaving 100 µl buffer in each well. Plates were then placed into a FLIPR™ instrument and were allowed to equilibrate at 37° C. Drug solution was added in a 50 µl volume to each well to give the desired final concentration. Cells were excited with an Argon laser at 488 nm, and emission was measured through a 510-570 nm bandwidth emission filter (FLIPR™, Molecular Devices, Sunnyvale, Calif.). The peak increase in fluorescence intensity was recorded for each well. On each plate, the standard agonist Prostaglandin E2 was tested over a $10^{-11}$ to $10^{-5}$ molar concentration range in the presence of vehicle or test drug. Concentration-effects were measured for Prostaglandin E2 in the presence of vehicle and test drug. A similar analysis was carried out for the other prostaglandin receptors, and for compound 2. The results are presented in Table 1, with the standard agonist for each assay listed in the Table.

TABLE 1

| Compound | hDP (HEK) | hEP$_1$ (HEK) | hEP$_2$ (HEK) | hEP$_{3A}$ (HEK) | hEP$_4$ (HEK) | hFP (HEK) | hIP (HEK) | hTP (HEK) |
|---|---|---|---|---|---|---|---|---|
| Standard agonist | 6 (BW245C) | 0.3 (PGE$_2$) | 2.5 (PGE$_2$) | 0.2 (PGE$_2$) | 0.2 (PGE$_2$) | 4.3 (PGF$_{2\alpha}$) | 62 (Carbacyclin) | 0.3 (U-46619) |
| Compound 1 | NA (K$_B$) | NA (K$_B$) | NA (K$_B$) | NA (K$_B$) | 101 (K$_B$) | NA (K$_B$) | NA (K$_B$) | NA (K$_B$) |
| Compound 2 | NA (K$_B$) | NA (K$_B$) | NA (K$_B$) | NA (K$_B$) | 172 (K$_B$) | NA (K$_B$) | NA (K$_B$) | NA (K$_B$) | hDP, hEP$_2$ and hEP$_4$ expressing cells coexpress chimeric G$_{qs5}$
hEP$_{3A}$ expressing cells coexpress chimeric G$_{qi5}$
NA: not active (at 10 µM); (% efficacy) for partial agonist; K$_B$ values are for antagonists (nM)

Example 24

A nasal spray comprising compound 1 is administered to a patient 5 times per day until the symptoms subside.

Example 25

A capsule comprising compound 2 is administered daily to a patient suffering from osteoporosis. Increase in bone density or reduction in bone density loss occurs for as long as the patient continues treatment.

Example 26

A tablet comprising compound 2 is administered to a person suffering from a migraine headache. Significantly less pain is experienced by the patient.

Example 27

A capsule or suppository comprising compound 1 is administered daily to a patient suffering from cancer. Improvement in the patient's condition occurs.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description. Such modifications are intended to fall within the scope of appended claims.

What is claimed is:

1. A method of treating an EP$_4$ receptor mediated condition comprising administering a therapeutically effective amount of a compound to a mammal in need thereof, wherein said compound has a formula

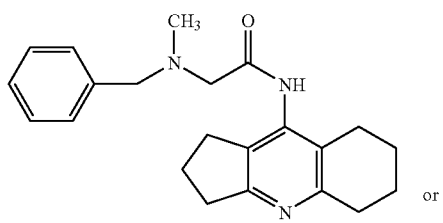

or

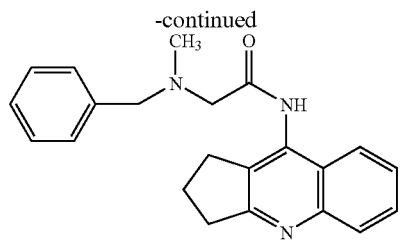

or a pharmaceutically acceptable salt thereof; and
wherein said EP$_4$ receptor mediated condition is an ocular disease, wherein said ocular disease is glaucoma.

2. A method comprising treating glaucoma by administering to a mammal suffering from glaucoma a compound comprising

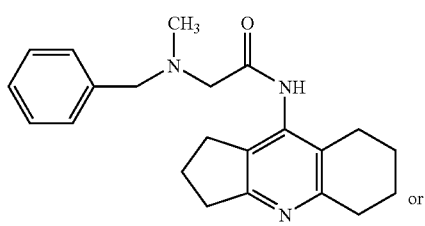

or

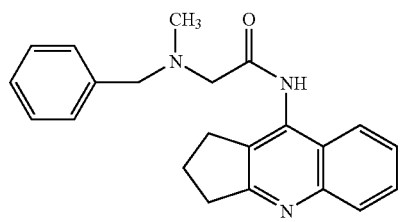

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,612,082 B2 | Page 1 of 1 |
| APPLICATION NO. | : 10/976442 | |
| DATED | : November 3, 2009 | |
| INVENTOR(S) | : Wheeler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1180 days.

Signed and Sealed this

Nineteenth Day of October, 2010

David J. Kappos
*Director of the United States Patent and Trademark Office*